(12) United States Patent
Kropf et al.

(10) Patent No.: US 6,316,030 B1
(45) Date of Patent: Nov. 13, 2001

(54) USE OF NANOSCALE STEROLS AND STEROL ESTERS

(75) Inventors: Christian Kropf, Duesseldorf; Thomas Foerster, Erkrath; Bernd Fabry, Korschenbroich; Martina Hollenbrock, Duesseldorf, all of (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/418,667

(22) Filed: Oct. 14, 1999

Related U.S. Application Data

(60) Provisional application No. 60/104,144, filed on Oct. 14, 1998.

(51) Int. Cl.$^7$ ............... A61K 9/14; A61K 9/00; A61K 7/00
(52) U.S. Cl. ............ 424/489; 424/426; 424/400; 424/401; 424/70.1
(58) Field of Search .................. 424/489, 426, 424/400, 401, 70.1; 252/309; 514/772.3

(56) References Cited

U.S. PATENT DOCUMENTS

| | | | |
|---|---|---|---|
| 4,115,313 | * | 9/1978 | Lyon et al. ............... 252/309 |
| 5,736,152 | * | 4/1998 | Dunn ...................... 424/426 |

FOREIGN PATENT DOCUMENTS

| | | |
|---|---|---|
| 1165574 | 3/1964 | (DE) . |
| 2024051 | 5/1986 | (DE) . |
| 0195311 | 3/1986 | (EP) . |
| 0693471 | 7/1995 | (EP) . |
| 0694521 | 7/1995 | (EP) . |
| 0818450 | 7/1997 | (EP) . |
| 0838155 | 10/1997 | (EP) . |
| 2252840 | 11/1974 | (FR) . |

OTHER PUBLICATIONS

R. Wachter, *Phytosterole—pflanzliche wirkstoffe in der Kosmetik*, Parf. Kosm. 75, 755(1994), pp. 755–761.

R. Wachter, *Phytosterols*, Cosm. Toil. 110, 72 (1995), pp. 72–80.

S. Chihlar, M. Tuerk, K. Schaber, *Micronization of Organic Solids by Rapid Expansion of Supercritical Solutions*, Proceedings World Congress on Particle Technology 3, Brighton, 1998, pp. 1–11.

H. Tronnier, G. Rentschler, *Experimentelle Untersuchungden zur Wirkungsweise aluminiumhaltiger Antiperspiranzien*, J.Soc.Cosm.Chem., 24, 281(1973) pp. 281–290.

A. Graham, M. Park, *Inhibition of the mitochondrial oxidation of octanoate by salicylic acid and related compounds*, J.Pharm.Pharmac., 26, 531(1975) pp. 531–534.

R. Lochhead, W. Fron, *Encyclopedia of Polymers and Thickeners for Cosmetics*, Cosm. Toil., 108, 95(1993), pp. 95–135.

P. Finkel, *Formulierung kosmetischer Sonnenschutzmittel*, SÖWF–Journal 122, 543(1996), pp. 543–548.

"Kosmetische Färbemittel" of the Farbstoffkommision der Deutschen Forschungsgemeinschaft, Verlag Chemie, Weinheim, 1984 pp. 81–106.

* cited by examiner

Primary Examiner—Thurman K. Page
Assistant Examiner—Blessing Fubara
(74) Attorney, Agent, or Firm—John E. Drach; Steven J. Trzaska

(57) ABSTRACT

A composition containing an effective amount of nanoparticles selected from the group consisting of nanoscale sterols, nanoscale sterol esters, and mixtures thereof.

17 Claims, No Drawings

USE OF NANOSCALE STEROLS AND STEROL ESTERS

CROSS-REFERENCE TO RELATED APPLICATIONS

This application claims priority from U. S. Provisional Application Ser. No. 60/104,144, filed Oct. 14, 1998, the disclosure of which is incorporated herein by reference.

BACKGROUND OF THE INVENTION

This invention relates generally to nanoparticles and more particularly to the use of nanoscale sterols and sterol esters in cosmetics.

Prior Art

Sterols and sterol esters are important raw materials both for cosmetics and pharmaceutical products and for the food industry. For example, it is known that sterols, especially vegetable representatives ("phytosterols"), are incorporated in the basal membrane of the skin and pass to the skin surface through the differentiation of the skin cells. This would explain the caring and protecting effect of phytosterols in skin cosmetics. The topical application of sterols also leads to an increased skin moisture level and to an increased lipid content. This improves the desquamation behavior of the skin and reduces any erythemas present. According to more recent studies, sterols (again preferably phytosterols) act on the arachidonic acid cascade by reducing the leucotriene level. However, high concentrations of leucotrienes in the skin are always accompanied by inflammatory reactions, as is the case for example with atopical dermatitis, psoriasis and UV erythemas. Accordingly, sterols also have an inflammation-inhibiting effect. In the field of skin care, sterol-containing preparations produce an improvement in combability and tear strength, especially in the case of bleached hair. Overviews on the properties of sterols and sterol esters in cosmetics have been published, for example, by R. Wachter in Parf. Kosm. 75, 755 (1994) and in Cosm. Toil. 110, 72 (1995). Reference is also made to German patent application DE-A1 19522822 (Henkel) which proposes mixtures of sterols and fatty alcohols for cosmetic applications. The antimicrobial effect of sterols and sterol derivatives is known, for example, from European patent application EP-A1 0 838 155 (Beiersdorf).

The effect of sterols and sterol esters is always associated with the rate at which the compounds are incorporated or absorbed. So far as the substances available at present are concerned, there is considerable potential for improvement in this regard. Accordingly, the problem addressed by the present invention was to accelerate the absorption of topically applied sterols and sterol esters by presenting them in new forms.

DESCRIPTION OF THE INVENTION

The present invention relates to the use of nanoscale sterols and/or sterol esters with particle diameters of 10 to 300 nm for the production of cosmetic and/or pharmaceutical preparations.

It has surprisingly been found that the absorption of sterols and sterol esters, particularly those based on vegetable raw materials, can be significantly increased if they are present in the form of nanoparticles, i.e. particles with a mean diameter of 10 to 300 and preferably 50 to 150 nm.

Sterols and Sterol Esters

Sterols (also known as stenols) are animal or vegetable steroids which only contain a hydroxyl group but no other functional groups at C-3. In general, sterols contain 27 to 30 carbon atoms and one double bond in the 5/6 position and occasionally in the 7/8, 8/9 or other positions. Besides these unsaturated species, other sterols are the saturated compounds obtainable by hydrogenation which are known as stanols and which are also encompassed by the present invention. One example of a suitable animal sterol is cholesterol. Typical examples of suitable phytosterols, which are preferred from the applicational point of view, are ergosterols, campesterols, stigmasterols, brassicasterols and, preferably, sitosterols or sitostanols and, more particularly, β-sitosterols or β-sitostanols. Besides the phytosterols mentioned, their esters are preferably used. The acid component of the ester may go back to carboxylic acids corresponding to formula (I):

$$R^1CO\text{—}OH \qquad (I)$$

in which $R^1CO$ is an aliphatic, linear or branched acyl group containing 2 to 22 carbon atoms and 0 and/or 1, 2 or 3 double bonds. Typical examples are acetic acid, propionic acid, butyric acid, valeric acid, caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, conjugated linoleic acid (CLA), linolenic acid, elaeosteric add, arachic acid, gadoleic acid, behenic acid and erucic acid and the technical mixtures thereof obtained, for example, in the pressure hydrolysis of natural fats and oils, in the reduction of aldehydes from Roelen's oxosynthesis or as monomer fraction in the dimerization of unsaturated fatty acids. Technical fatty acids containing 12 to 18 carbon atoms, for example cocofatty acid, palm oil fatty acid, palm kernel oil fatty acid or tallow fatty acid, are preferred. It is particularly preferred to use esters of β-sitosterol or β-sitostanol with fatty acids containing 12 to 18 carbon atoms. These esters may be prepared both by direct esterification of the phytosterols with the fatty acids or by transesterification with fatty acid lower alkyl esters or triglycerides in the presence of suitable catalysts, for example sodium ethylate or, more particularly, enzymes [cf. EP-A2 0195311 (Yoshikawa)].

Production of Nanoparticles

One process for the production of nanoparticles by rapid expansion of supercritical solutions (RESS) is known from the article by S. Chihlar, M. Türk and K Schaber in Proceedings World Congress on Particle Technology 3, Brighton, 1998. To prevent the nanoparticles from agglomerating, it is advisable to dissolve the starting materials in the presence of suitable protective colloids or emulsifiers and/or to expand the critical solutions into aqueous and/or alcoholic solutions of the protective colloids or emulsifiers or into cosmetic oils which may in turn contain redissolved emulsifiers and/or protective colloids. Suitable protective colloids are, for example, gelatine, casein, gum arabic, lysalbinic acid, starch and polymers, such as polyvinyl alcohols, polyvinyl pyrrolidones, polyalkylene glycols and polyacrylates. Accordingly, the nanoscale sterols and/or sterol esters preferably used are those which are surrounded by a protective colloid and/or an emulsifier. The protective colloids or emulsifiers are normally used in quantities of 0.1 to 20% by weight and preferably in quantities of 5 to 15% by weight, based on the sterols or sterol esters.

Another suitable process for the production of nanoscale particles is the evaporation technique. Here, the starting materials are first dissolved in a suitable organic solvent (for example alkanes, vegetable oils, ethers, esters, ketones, acetals and the like). The resulting solutions are then introduced into water or another non-solvent, optionally in the presence of a surface-active compound dissolved therein, in such a way that the nanoparticles are precipitated by the homogenization of the two immiscible solvents, the organic solvent preferably evaporating. O/w emulsions or o/w microemulsions may be used instead of an aqueous solution. The emulsifiers and protective colloids mentioned at the beginning may be used as the surface-active compounds. Another method for the production of nanoparticles is the so-called GAS process (gas anti-solvent recrystallization). This process uses a highly compressed gas or supercritical fluid (for example carbon dioxide) as non-solvent for the crystallization of dissolved substances. The compressed gas phase is introduced into the primary solution of the starting materials and absorbed therein so that there is an increase in the liquid volume and a reduction in solubility and fine particles are precipitated. The PCA process (precipitation with a compressed fluid ant-solvent) is equally suitable. In this process, the primary solution of the starting materials is introduced into a supercritical fluid which results in the formation of very fine droplets in which diffusion processes take place so that very fine particles are precipitated. In the PGSS process (particles from gas saturated solutions), the starting materials are melted by the introduction of gas under pressure (for example carbon dioxide or propane). Temperature and pressure reach near- or super-critical conditions. The gas phase dissolves in the solid and lowers the melting temperature, the viscosity and the surface tension. On expansion through a nozzle, very fine particles are formed as a result of cooling effects.

Commercial Applications

Compared with conventional sterols and sterol esters, the particular fineness of the particles provides for their more rapid penetration into the stratum corneum after topical application. The nanoscale compounds are normally used in a quantity of 0.1 to 5% by weight, preferably in a quantity of 0.5 to 3% by weight and more preferably in a quantity of 1 to 2% by weight, based on the preparations.

Cosmetic and/or Pharmaceutical Preparations

The preparations obtainable using the nanoscale sterols and sterol esters in accordance with the invention, such as for example hair shampoos, hair lotions, foam baths, cremes, lotions or emollients, may contain mild surfactants, oils, emulsifiers, superfatting agents, pearlescing waxes, stabilizers, consistency regulators, thickeners, polymers, silicone compounds, biogenic agents, deodorizers, anti-dandruff agents, film-formers, preservatives, hydrotropes, solubilizers, sun (UV) protection factors, antioxidants, insect repellents, self-tanning agents, perfume oils, dyes and the like as further auxiliaries and additives.

Typical examples of suitable mild, i.e. dermatologically compatible, surfactants, are fatty alcohol polyglycol ether sulfates, monoglyceride sulfates, mono- and/or dialkylsulfosuccinates, fatty acid isethionates, fatty acid sarcosinates, fatty acid taurides, fatty acid glutamates, ether carboxylic acids, alkyl oligoglucosides, fatty acid glucamides, alkyl amidobetaines and/or protein fatty acid condensates (preferably based on wheat proteins).

Suitable oils are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of hydroxycarboxylic acids with linear or branched $C_{6-22}$ fatty alcohols, more particularly dioctyl malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons. These oils may even be used in the production of the nanoparticles where they serve as the medium into which the fluid solutions are expanded.

Suitable emulsifiers are, for example, nonionic surfactants from at least one of the following groups:

(1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group;

(2) $C_{12/18}$ fatty acid monoesters and diesters of adducts of 1 to 30 moles of ethylene oxide with glycerol;

(3) glycerol monoesters and diesters and sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) adducts of 15 to 60 moles of ethylene oxide with castor oil and/or hydrogenated castor oil;

(6) polyol esters and, in particular, polyglycerol esters such as, for example, polyglycerol polyricinoleate, polyglycerol poly-12-hydroxy-stearate or polyglycerol dimerate. Mixtures of compounds from several of these classes are also suitable;

(7) adducts of 2 to 15 moles of ethylene oxide with castor oil and/or hydro-genated castor oil;

(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) mono-, di- and trialkyl phosphates and mono-, di- and/or tri-PEG-alkyl phosphates and salts thereof;

(10) wool wax alcohols;

(11) polysiloxane/polyalkyl polyether copolymers and corresponding derivatives;

(12) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol or polyglycerol, and

(13) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

$C_{8/18}$ alkyl mono- and oligoglycosides, their production and their use are known from the prior art. They are produced in particular by reacting glucose or oligosaccharides with primary alcohols containing 8 to 18 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based.

Typical examples of anionic emulsifiers are soaps, alkylbenzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccina-mates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow range homolog distribution.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example coco-acylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Coco-amidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$acyl sarcosine. Besides ampholytic emulsifiers, quaternary emulsifiers may also be used, those of the esterquat type, preferably methyl-quaternized difatty acid triethanolamine ester salts, being particularly preferred.

Like the oils, the nonionic, anionic, cationic or amphoteric or zwitterionic emulsifiers mentioned may serve as co-solvents or as media into which the fluid mixtures are expanded.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlescing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency regulators mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryidimonium Hydroxypropyl Hydrolyzed Collagen (Lamequat® L, Grünau GmbH), quaternized wheat polypeptides, polyethyleneimine, cationic silicone polymers such as, for example, Amidomethicone, copolymers of adipic acid and dimethylaminohy-droxypropyl diethylenetriamine (Cartaretine®, Sandoz AG), copolymers of acrylic acid with dimethyl diallyl ammonium chloride (Merquat® 550, Chemviron), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromo-butane, with bisdialkylamines, for example bisdimethylamino-1,3-propane, cationic guar gum such as, for example, Jaguar®CBS, Jaguar®C-17, Jaguar®C-16 of Celanese, USA, quaternized ammonium salt polymers such as, for example, Mirapol® A-15, Mirapol® AD-1, Mirapol® AZ-1 of Miranol, USA.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. In addition, a detailed review of suitable liquid silicones was published by Todd et al. in Cosm. Toil. 91, 27 (1976).

Typical examples of fats are glycerides while suitable waxes are inter alia beeswax, carnauba wax, candelilla wax, montan wax, paraffin wax or microwaxes, optionally in combination with hydrophilic waxes, for example cetyl stearyl alcohol or partial glycerides. Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts, and vitamin complexes.

Suitable deodorizers are, for example, antiperspirants, such as aluminium chlorhydrates. These antiperspirants are colorless hygroscopic crystals which readily deliquesce in air and which accumulate when aqueous aluminium chloride solutions are concentrated by evaporation. Aluminium chlorhydrate is used for the production of perspiration-inhibiting and deodorizing formulations and probably acts by partially blocking the sweat glands through the precipitation of proteins and/or polysaccharides [cf. J. Soc. Cosm. Chem. 24, 281 (1973)]. For example, an aluminium chlorhydrate which corresponds to the formula $[Al_2(OH)_5Cl].2.5H_2O$ and which is particularly preferred for the purposes of the invention is commercially available under the name of Locron® from Hoechst AG of Frankfurt, FRG [cf. J. Pharm. Pharmcol. 26, 531 (1975)]. Besides the chlorhydrates, aluminium hydroxylactates and acidic aluminium/zirconium salts may also be used. Other suitable deodorizers are esterase inhibitors, preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in stick products. Examples of such antibacterial agents are chitosan, phenoxyethanol and chlorhexidine gluconate. 5-Chloro-2-(2,4-dichlorophenoxy)-phenol, which is marketed under the name of Irgasan® by Ciba-Geigy of Basel, Switzerland, has also proved to be particularly effective.

Suitable antidandruff agents are climbazol, octopirox and zinc pyrethion. Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases are montmorillonites, clays minerals, Pemulen and alkyl-modified Carbopol types (Goodrich). Other suitable polymers and swelling agents can be found in R. Lochhead's review in Cosm. Toil. 108, 95 (1993).

Sun (UV) protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP-B1 0693471;

4-aminobenzoic acid derivatives, preferably 4-(dimethylamino)-benzoic acid-2-ethylhexyl ester, 4-dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone as described in EP-A1 0818450;

propane-1,3-diones such as, for example, 1-(4-tert.butylphenyl)-3-(4'-methoxyphenyl)-propane-1,3-dione;

ketotricyclo(5.2.1.0)decane derivatives as described in EP-B1 0694521.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione, 4-tert.butyl4'-methoxydibenzoyl methane (Parsol 1789) or 1-phenyl-3-(4'-isopropylphenyl)-propane-1,3dione. The UV-A and UV-B filters may of course also be used in the form of mixtures. Besides the soluble substances mentioned, insoluble light-blocking pigments, i.e. finely dispersed metal oxides or salts, for example titanium dioxide, zinc oxide, iron oxide, aluminium oxide, cerium oxide, zirconium oxide, silicates (talcum), barium sulfate and zinc stearate, may also be used for this purpose. The particles should have a mean diameter of less than 100 nm, preferably between 5 and 50 nm and more preferably between 15 and 30 nm. They may be spherical in shape although ellipsoidal particles or other non-spherical particles may also be used. Other suitable UV filters can be found in P. Finkel's review in S ÖFW-Journal 122, 543 (1996).

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg) also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, ZnSO$_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes, for example ethanol, isopropyl alcohol or polyols, may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, iso-E-Super, Fixolide NP, evernyl, iraldein gamma, phenylacetic acid, geranyl acetate, benzyl acetate, rose oxide, romillate, irotyl and floramate.

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be produced by standard hot or cold processes and are preferably produced by the phase inversion temperature method.

EXAMPLES

To prepare the nanoscale sterols and sterol esters (Examples 1 to 5), carbon dioxide was taken from a reservoir under a constant pressure of 60 bar and purified in a column with an active carbon packing and a molecular sieve packing. After liquefaction, the $CO_2$ was compressed to the required supercritical pressure p by means of a diaphragm pump at a constant delivery rate of 3.5 l/h. The solvent was then brought to the necessary temperature T1 in a preheater and introduced into an extraction column (steel, 400 ml) which had been charged with the sterol or sterol ester. The resulting supercritical, i.e. fluid, mixture was sprayed through a laser-drawn nozzle (length 830 μm, diameter 45 μm) at a temperature T2 into a Plexiglas expansion chamber which contained a 4% by weight aqueous solution of an emulsifier or protective colloid. The fluid medium evaporated, leaving the nanoparticles dispersed in the protective colloid behind. To produce the nanoparticles of Example 6, a 1% by weight solution of phytosterol in acetone was added dropwise to a 4% by weight aqueous solution of Coco Glucosides with vigorous stirring at 40° C. under a reduced pressure of 40 mbar. The evaporating solvent was condensed in a cold trap while the dispersion containing the nanoparticles remained behind. The process conditions and the mean particle size range (as determined photometrically by the 3-WEM method) are shown in Table 1 below.

TABLE 1

Nanoparticles

| Ex. | Sterol/Sterol Ester | Solv. | p bar | T1 °C. | T2 °C. | Emulsifier/Protective Colloid | PSR nm |
|---|---|---|---|---|---|---|---|
| 1 | Phytosterol* | $CO_2$ | 200 | 80 | 175 | Polyvinyl alcohol | 50–125 |
| 2 | Phytosterol* | $CO_2$ | 180 | 70 | 160 | Polyethylene glycol (M = 400) | 70–130 |
| 3 | β-Sitostanol | $CO_2$ | 200 | 85 | 180 | Polyvinyl alcohol | 70–140 |
| 4 | β-Sitostenyl laurate | $CO_2$ | 200 | 85 | 175 | Polyvinyl alcohol | 50–150 |
| 5 | β-Sitostanyl stearate | $CO_2$ | 200 | 85 | 175 | Coco Glucosides | 50–150 |
| 6 | Phytosteroil* | — | — | — | — | Coco Clucosides | 65–140 |

*58.1% by weight β-sitosterol, 29.8% by weight campesterol, 4.5% by weight stigmasterol; 3.8% by weight tocopherol; 0.4% by weight cholesterol; 0.3% by weight squalane; unsaponifiables to 100

Table 2 below contains a number of Formulation Examples using phytosterol nanoparticles.

TABLE 2

Cosmetic preparations (water, preservative to 100% by weight)

| Composition (INCI) | 1 | 2 | 3 | 4 | 5 | 6 | 7 | 8 | 9 | 10 |
|---|---|---|---|---|---|---|---|---|---|---|
| Dehymuls ® PGPH Polyglyceryl-2-Dipolyhydroxystearate | 2.0 | 3.0 | — | 5.0 | — | — | — | — | — | — |
| Lameform ® TGI Polyglyceryl-3-Diisostearate | 4.0 | 1.0 | — | — | — | — | — | — | — | — |
| Ambi ® EM 90 Cetyl Dimethicone Copolyol | — | — | 3.0 | — | — | — | — | — | — | — |
| Emulgade ® PL 68/50 Cetearyl Glucoside (and) Cetearyl Alcohol | — | — | — | — | 4.0 | — | — | — | 3.0 | — |
| Eumulgin ® B2 Ceteareth-20 | — | — | — | — | — | — | — | 2.0 | — | — |
| Tegocare ® PS Polyglyceryl-3 Methylglucose Distearate | — | — | — | — | — | — | 4.0 | — | — | — |
| Eumulgin VL ® 75 Polyglyceryl-2 Dipolyhydroxy stearate (and) Lauryl Glucoside (and) Glycerin | — | — | — | — | — | 3.5 | — | — | 2.5 | — |
| Bees Wax | 3.0 | 2.0 | 5.0 | 2.0 | — | — | — | — | — | — |
| Cutina ® GMS Glyceryl Stearate | — | — | — | — | — | 2.0 | 4.0 | — | — | 4.0 |
| Lanette ® O Cetearyl Alcohol | — | — | 2.0 | — | 2.0 | 4.0 | 2.0 | 4.0 | 4.0 | 1.0 |
| Antaron ® V 216 PVP/Hexadecene Copolymer | — | — | — | — | — | 3.0 | — | — | — | 2.0 |
| Plantaren ® 818 Cocoglycerides | 5.0 | — | 10.0 | — | 8.0 | 6.0 | 6.0 | — | 5.0 | 5.0 |
| Finsolv ® TN C12/15 Alkyl Benzoate | — | 6.0 | — | 2.0 | — | — | 3.0 | — | — | 2.0 |
| Dioctyl Carbonate | 5.0 | 4.0 | 6.0 | 8.0 | 6.0 | 5.0 | 4.0 | 3.0 | 4.0 | 6.0 |
| Cetiol ® J 600 Oleyl Erucate | 2.0 | — | 3.0 | 5.0 | 4.0 | 3.0 | 3.0 | — | 5.0 | 4.0 |
| Cetiol ® OE Dicaprylyl Ether | 3.0 | — | — | — | — | 1.0 | — | — | — | — |
| Mineral Oil | — | 4.0 | — | 4.0 | — | 2.0 | — | 1.0 | — | — |
| Cetiol ® PGL Hexadecanol (and) Hexyldecyl Laurate | — | 7.0 | 3.0 | 7.0 | 4.0 | — | — | — | 1.0 | — |
| Panthenol/Bisabolol | 1.2 | 1.2 | 1.2 | 1.2 | 1.2 | 1.2 | 1.2 | 1.2 | 1.2 | 1.2 |
| Nano-Phytosterol | 0.5 | 1.0 | 1.0 | 2.0 | 1.0 | 1.0 | 1.0 | 2.0 | 0.5 | 2.0 |

TABLE 2-continued

| (Example 1) | | | | | | | | | | |
|---|---|---|---|---|---|---|---|---|---|---|
| Neo Heliopan ® Hydro<br>Sodium Phenylbenzimidazole Sulfonate | 3.0 | — | — | 3.0 | — | — | 2.0 | — | 2.0 | — |
| Neo Heliopan ® 303<br>Octocrylene | — | 5.0 | — | — | — | 4.0 | 5.0 | — | — | 10.0 |
| Neo Heliopan ® BB<br>Benzophenon-3 | 1.5 | — | — | 2.0 | 1.5 | — | — | — | 2.0 | — |
| Neo Heliopan ® E 100<br>Isoamyl p-Methoxycinnamate | 5.0 | — | 4.0 | — | 2.0 | 2.0 | 4.0 | 10.0 | — | — |
| Neo Heliopan ® AV<br>Octyl Methoxycinnamate | 4.0 | — | 4.0 | 3.0 | 2.0 | 3.0 | 4.0 | — | 10.0 | 2.0 |
| Uvinul ® T 150<br>Octyl triazone | 2.0 | 4.0 | 3.0 | 1.0 | 1.0 | 1.0 | 4.0 | 3.0 | 3.0 | 3.0 |
| Zinc Oxide | — | 6.0 | 6.0 | — | 4.0 | — | — | — | — | 5.0 |
| Titanium Dioxide | — | 2.0 | 2.0 | — | — | — | — | 5.0 | — | — |
| Glycerin (86% by weight) | 5.0 | 5.0 | 5.0 | 5.0 | 5.0 | 5.0 | 5.0 | 5.0 | 5.0 | 5.0 |

| Composition (INCI) | 11 | 12 | 13 | 14 | 15 | 16 | 17 | 18 | 19 | 20 |
|---|---|---|---|---|---|---|---|---|---|---|
| Texapon ® NSO<br>Sodium Laureth Sulfate | — | 30.0 | — | — | 25.0 | — | — | — | — | — |
| Plantacare ® 818<br>Coco Glucosides | — | 10.0 | 30.0 | — | 20.0 | — | — | — | — | — |
| Plantacare ® PS 10<br>Sodium Laureth Sulfate (and) Coco Glucosides | 22.0 | — | — | 22.0 | — | — | — | — | — | — |
| Dehyton ® PK 45<br>Cocamidopropyl Betaine | 15.0 | 10.0 | 10.0 | 15.0 | 20.0 | — | — | — | — | — |
| Emulgade ® SE<br>Glyceryl Stearate (and) Ceteareth 12/20 (and) Cetearyl Alcohol (and) Cetyl Palmitate | — | — | — | — | — | 5.0 | 5.0 | — | — | — |
| Eumulgin ® B1<br>Ceteareth-12 | — | — | 15.0 | — | — | — | — | — | — | — |
| Eumulgin ® HRE 60<br>PEG 60 Hydrogenated Caster Oil | — | — | — | — | 5.0 | — | — | — | — | — |
| Lameform ® TGI<br>Polyglycaryl-3 Isostearate | — | — | — | — | — | — | — | 4.0 | 4.0 | 4.0 |
| Dehymuls ® PGPH<br>Polyglyceryl-2 Dipolyhydroxystearate | — | — | 3.8 | — | — | — | — | — | — | — |
| Monomuls ® 90-O 18<br>Glyceryl Oleate | — | — | — | — | — | — | — | 2.0 | 2.0 | 2.0 |
| Cetiol ® HE<br>PEG-7 Glyceryl Cocoate | 2.0 | — | — | 2.0 | 5.0 | — | — | — | — | — |
| Cetiol ® OE<br>Dicaprylyl Ether | — | — | — | — | — | — | — | 5.0 | 5.0 | 5.0 |
| Cetioil ® PGL<br>Hexyldecanol (and) Hexyldecyl Laurate | — | — | — | — | — | — | — | 10.0 | 10.0 | 10.0 |
| Cetiol ® SN<br>Ceteary Isononanoate | — | — | — | — | — | 3.0 | 3.0 | — | — | — |
| Cetiol ® V<br>Decyl Oleate | — | — | — | — | — | 3.0 | 3.0 | — | — | — |
| Myritol ®318<br>Coco Caprylate Caprate | — | — | — | — | — | — | — | 5.0 | 5.0 | 10.0 |
| Melissa oil | — | — | 5.0 | — | — | — | — | — | — | — |
| Bees Wax | — | — | — | — | — | — | — | 7.0 | 7.0 | 7.0 |
| Nutrilan ® Keratin W<br>Hydrolyzed Keratin | — | — | — | — | — | 40.0 | 60.0 | — | — | — |
| Nutrilan ® I<br>Hydrolyzed Collagen | — | — | — | — | 2.0 | — | — | — | — | — |
| Lamesoft ® LMG<br>Glyceryl Laurate (and) Potassium Cocoyl Hydrolyzed Collagen | — | 4.0 | — | — | — | — | — | — | — | — |
| Gluadin ® AGP<br>Hydrolyzed Wheat Gluten | 0.5 | 0.5 | — | — | — | — | — | 5.0 | — | — |
| Gluadin ® WK<br>Sodium Cocoyl Hydrolyzed Wheat Protein | 2.0 | 2.0 | 4.0 | 2.0 | 5.0 | — | — | — | 5.0 | 5.0 |
| Nano-Phytosterol (Example 1) | 0.5 | 1.0 | 1.0 | 2.0 | 1.0 | 1.0 | 1.0 | 2.0 | 2.0 | 2.0 |
| Euperlan ® PK 3000 AM<br>Glycol Distearate (and) Laureth-4 (and) Cocamidopropyl Betaine | 5.0 | — | — | 5.0 | — | — | — | — | — | — |
| Arlypon ® F<br>Laureth-2 | — | — | 1.5 | — | — | — | — | — | — | — |
| Magnesium Sulfate Heptahydrate | — | — | — | — | — | — | — | 1.0 | 1.0 | 1.0 |
| Glycerin (86% by weight) | — | — | — | — | — | 3.0 | 3.0 | 5.0 | 5.0 | 5.0 |

(1) w/o sun protection creame,
(2–4) w/o sun protection lotion,
(5,8,10) o/w sun protection lotion, TABLE 2-continued (6,7,9) o/w sun protection creme
(11–15) foam bath,
(16) soft creme,
(17) moisturizing emulsion,
(18–20) night creme

What is claimed is:

1. A composition comprising an effective amount of nanoparticles selected from the group consisting of nanoscale sterols, nanoscale sterol esters, and mixtures thereof.

2. A. The composition of claim 1 wherein the nanoscale sterols and nanoscale sterol esters are phytosterols and their ester derivatives.

3. The composition of claim 1 wherein the nanoscale sterols and nanoscale sterol esters are sitosterols and their ester derivatives.

4. The composition of claim 1 wherein the nanoparticles are surrounded by a medium selected from the group consisting of a protective colloid, and emulsifier and mixtures thereof.

5. The composition of claim 4 wherein the medium is present in an amount of from 0.1 to 20% by weight, based on the weight of the nanoparticle.

6. The composition of claim 4 wherein the medium is a protective colloid selected from the group consisting of polyvinyl alcohol, polyethylene glycol, and mixtures thereof.

7. The composition of claim 1 wherein the nanoparticles are present in the composition in an amount of from 0.1 to 5% by weight, based on the weight of the composition.

8. A process for making nanoscale sterols, and their ester derivatives, comprising:
   (a) providing a starting material selected from the group consisting of sterols, sterol esters, and mixtures thereof;
   (b) providing a solvent;
   (c) dissolving the starting material in the solvent under supercritical or near-critical conditions to form a fluid mixture;
   (d) expanding the fluid mixture through a nozzle and into a vacuum, gas or liquid; and
   (e) simultaneously evaporating the solvent from the fluid mixture as it expands, to form the nanoscale sterols and their ester derivatives.

9. The process of claim 8 wherein the sterols are phytosterols.

10. The process of claim 8 wherein the sterols are sitosterols.

11. A process for treating human skin or hair comprising:
    (a) providing a composition containing an effective amount of nanoparticles selected from the group consisting of nanoscale sterols, nanoscale sterol esters, and mixtures thereof; and
    (b) applying the composition onto human skin or hair.

12. The process of claim 11 wherein the nanoscale sterols and nanoscale sterol esters are phytosterols and their ester derivatives.

13. The process of claim 11 wherein the nanoscale sterols and nanoscale sterol esters are sitosterols and their ester derivatives.

14. The process of claim 11 wherein the nanoparticles are surrounded by a medium selected from the group consisting of a protective colloid, and emulsifier, and mixtures thereof.

15. The process of claim 14 wherein the medium is present in an amount of from 0.1 to 20% by weight, based on the weight of the nanoparticle.

16. The process of claim 14 wherein the medium is a protective colloid selected from the group consisting of polyvinyl alcohol, polyethylene glycol, and mixtures thereof.

17. The process of claim 11 wherein the nanoparticles are present in the composition in an amount of from 0.1 to 5% by weight, based on the weight of the composition.

* * * * *